(12) United States Patent
Syage et al.

(10) Patent No.: US 8,614,582 B2
(45) Date of Patent: Dec. 24, 2013

(54) METHOD OF SIMULTANEOUSLY SCREENING A PLURALITY OF PEOPLE

(75) Inventors: Jack A. Syage, Huntington Beach, CA (US); Karl A. Hanold, Huntington Beach, CA (US)

(73) Assignee: Morpho Detection, Inc., Newark, CA (US)

( * ) Notice: Subject to any disclaimer, the term of this patent is extended or adjusted under 35 U.S.C. 154(b) by 963 days.

(21) Appl. No.: 12/082,535

(22) Filed: Apr. 10, 2008

(65) Prior Publication Data
US 2011/0181288 A1    Jul. 28, 2011

(51) Int. Cl.
*G01N 9/00*    (2006.01)

(52) U.S. Cl.
USPC ............................ 324/464; 73/23.2; 73/31.02

(58) Field of Classification Search
None
See application file for complete search history.

(56) References Cited

U.S. PATENT DOCUMENTS

| | | | |
|---|---|---|---|
| 4,045,997 A * | 9/1977 | Showalter et al. | 73/23.2 |
| 5,915,268 A | 6/1999 | Linker et al. | |
| 6,073,499 A | 6/2000 | Settles | |
| 6,345,545 B1 | 2/2002 | Linker et al. | |
| 6,708,572 B2 | 3/2004 | Jenkins et al. | |
| 7,141,786 B2 * | 11/2006 | McGann et al. | 250/287 |
| 7,401,498 B2 * | 7/2008 | Syage et al. | 73/28.01 |
| 2006/0049346 A1 * | 3/2006 | McGann et al. | 250/287 |
| 2006/0196249 A1 * | 9/2006 | Syage et al. | 73/31.07 |

* cited by examiner

*Primary Examiner* — Vinh Nguyen
(74) *Attorney, Agent, or Firm* — Armstrong Teasdale LLP

(57) ABSTRACT

A detector system with a portal including a plurality of output ports that direct a plurality of output airstreams in an essentially horizontal direction, and a plurality of intake ports that pull in air. The system also includes at least one concentrator coupled to at least one of the intake ports, and a detector coupled to the concentrator. The horizontally oriented output airstreams and multiple intake ports provide a system that can rapidly screen multiple people for explosives and other substances.

6 Claims, 9 Drawing Sheets

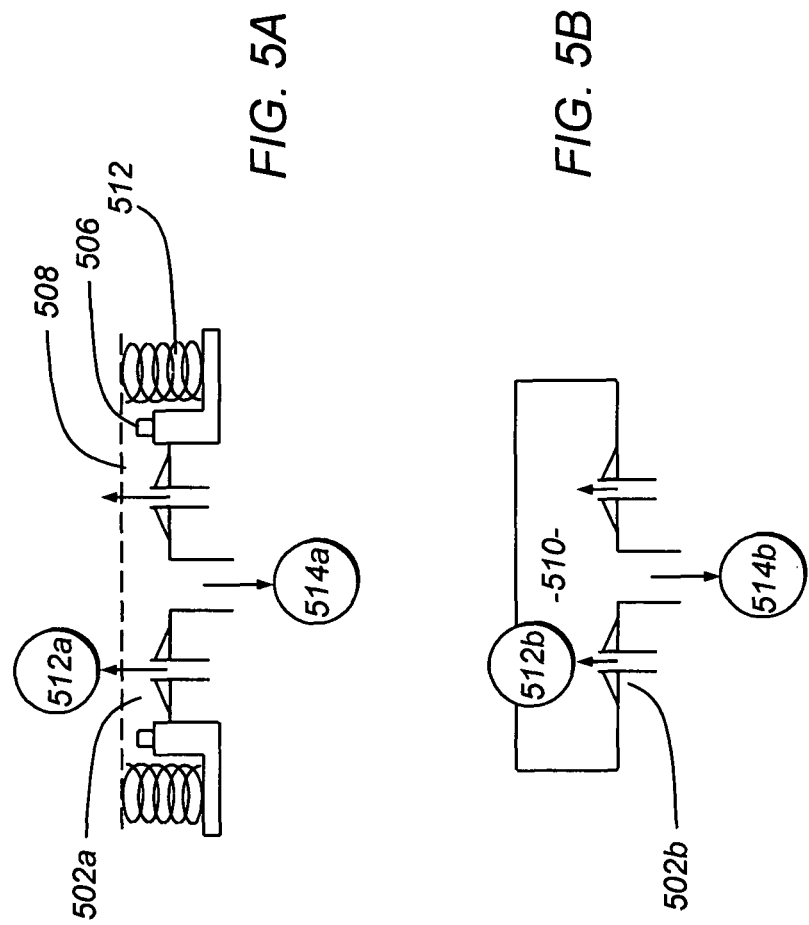

METHOD OF SIMULTANEOUSLY SCREENING A PLURALITY OF PEOPLE

BACKGROUND OF THE INVENTION

1. Field of the Invention

The present invention relates to the field of detection apparatus used to screen individuals for the presence of explosives and other chemical entities.

2. Background Information

Security threats to the public dictate development of new technologies capable of rapidly detecting the presence of illicit and hazardous materials. Lead organizations such as the Department of Homeland Security (DHS) and the Transportation Security Agency (TSA) are responsible for ensuring safety of air travel and have invested significantly in developing technologies to combat the potential for attacks by explosive devices. Other venues that require screening include customs and port security. There is also a desire to screen other illicit materials such as drugs.

There are primarily two types of detectors used for screening baggage and people, explosive detection systems (EDSs) and explosives trace detectors (ETDs). Explosive detection systems (EDSs) detect bulk explosives hidden in checked baggage and frequently operate using dual x-ray tomography. Explosives trace detectors (ETDs) detect vapor or particles of explosives that are contaminated on people and the surface of baggage. ETDs are also used to resolve alarms from EDSs. Currently ETDs are used on a selective basis to screen for personal items and carry-on bags, but not for directly screening individuals. The lack of a capability to screen for explosives hidden on an individual is arguably the greatest vulnerability in aviation and homeland security. Though most of the attention for explosives threat detection is focused on aviation security, in fact security is an issue for many venues including other types of transportation, buildings, ports, stadiums, military bases and field operations, and in general any high traffic environment.

Personnel screening portals have been developed to screen individuals for concealed explosives and other materials. Several portal concepts using ETDs have been developed and tested and are referred to as explosives trace portals (ETPs). The most promising are based on non-intrusive (non-contact) removal of particles from clothing, followed by high-flow collection of the particles on the surface of a mesh or substrate; and then thermal desorption into an ETD. For example, U.S. Pat. No. 5,915,268 issued to Linker discloses a portal device that uses air jets to dislodge particles from a person and a downward flow of air to entrain and carry the particles to a concentrator device.

U.S. Pat. No. 6,073,499 issued to Settles discloses a passive method of particle collection that relies on the upward flow of air around people due to thermal conductivity in what is called a human thermal plume (HTP).

U.S. Pat. No. 6,708,572 issued to Jenkins discloses a similar method that uses air jets to assist the upward flow of the HTP. Each of these portal methods involve a flow of particle and vapor laden air and uses a concentration device that removes the target particles and vapor from the large volume of air by collecting them onto a mesh or substrate. The target particles and vapor are then thermally desorbed and mixed with a low volume flow of gas that leads to a chemical analyzer.

A two-stage concentrator for vapor/particle detection was disclosed by Linker and U.S. Pat. No. 6,345,545 issued to Brusseau. The two-stage concentrator enables concentrating particles in a high-volume gas flow to be efficiently coupled to a detector. The first stage of the concentrator contains a metal mesh for collecting particles and vapor that are entrained in the high-volume gas flow. The desorbed vapors from the first-stage concentrator are collected on the second-stage concentrator and provided to the detectors with a low-volume gas flow.

U.S. Pat. Appl. 2006/0196249 filed in the name of Syage and Hanold discloses a portal that screens multiple people with a single detector. In this configuration the process of collecting sample from people and transferring it to a concentrator are independent of the transfer of the sample from the concentrator to the detector. With this approach, sample can be effectively stored on a concentrator until the detector is ready to analyze it.

The chemical detectors used in all of the portals mentioned above use some form of ETDs including ion mobility spectrometry (IMS), mass spectrometry (MS), and gas chromatography/chemiluminescence (GC/CL) detectors. Other detectors may also be used.

An important characteristic of a personnel screening portal is fast operation to maximize the number of people screened by the portal. Current portals operate with a sampling interval of about 10-20 seconds from one person to another. This is much longer than the interval for standard metal detectors which range between 4-6 seconds. Methods to improve the sampling interval of a vapor/particle detecting portal are highly desirable.

It is also important that portals have reasonable upfront and recurring costs per unit. Given the large number of passenger lanes in U.S. and international airports (about 3000 each) and limited available budgets, inevitable compromises are made with regard to cost and the number of units that can be deployed. Furthermore current portals do not have the throughput capacity to handle other high flow transportation environments such as train and subways systems, and bus systems. Solutions that reduce the cost per passenger screened would allow greater distribution of deployed screening portals.

BRIEF SUMMARY OF THE INVENTION

A detector system with a portal including a plurality of output ports that direct a plurality of output airstreams in an essentially horizontal direction, and a plurality of intake ports that pull in air. The system also includes at least one concentrator coupled to at least one of the intake ports, and a detector coupled to the concentrator.

BRIEF DESCRIPTION OF THE DRAWINGS

FIG. 5A is an illustration of an embodiment of a hand screener that includes a spring loaded activated sampling grid;

FIG. 5B is an illustration of another embodiment of the hand screener;

DETAILED DESCRIPTION

Figure 1:
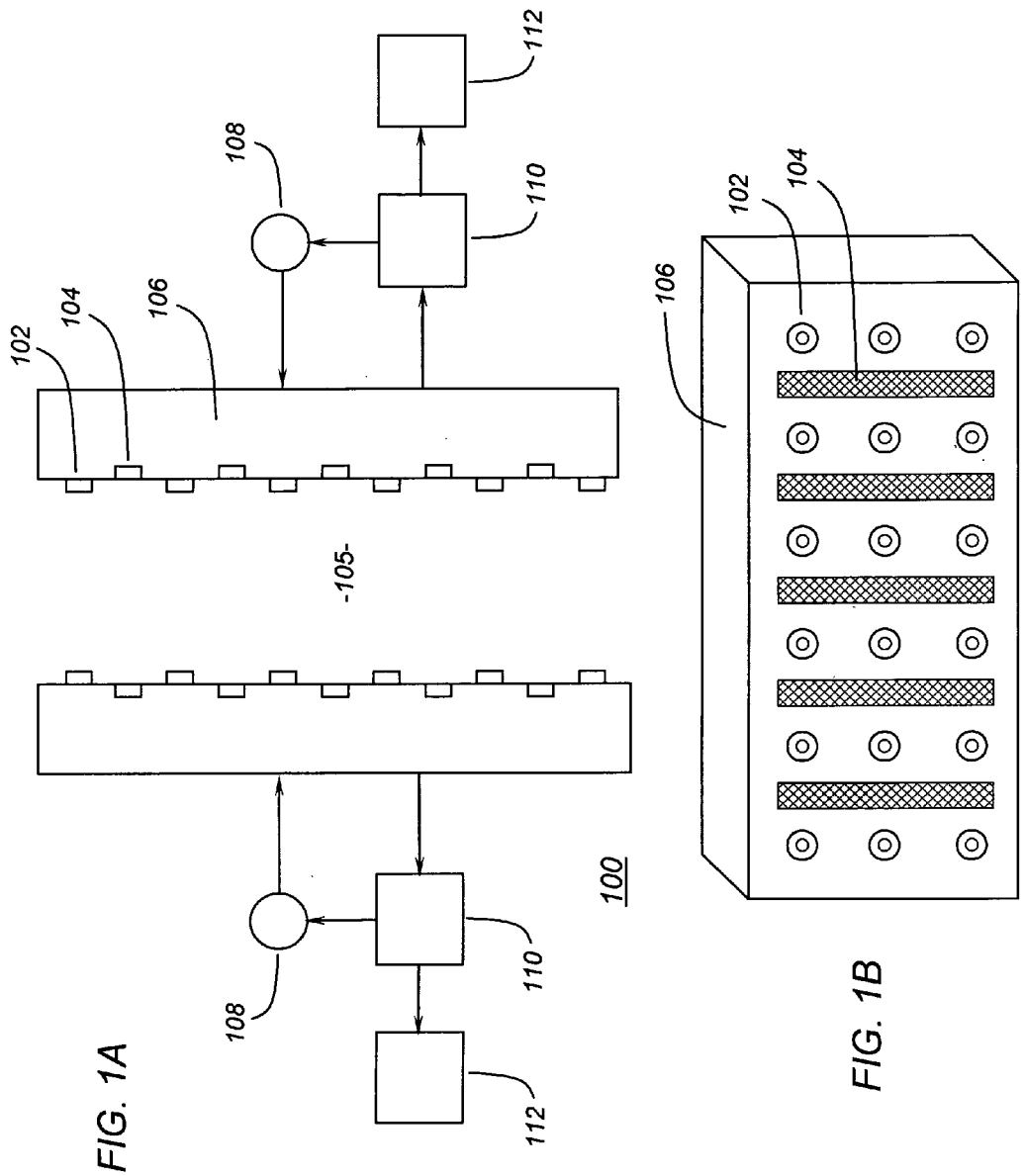
FIG. 1A is a top view showing a walk-through passageway that screens people for explosives using air jets and intake ports.
FIG. 1B is a perspective view of one side of the explosives detecting passage way showing a configuration of air jet nozzles and intake manifolds.

Disclosed is a detector system with a portal including a plurality of output ports that direct a plurality of output airstreams in an essentially horizontal direction, and a plurality of intake ports that pull in air. The system also includes at least one concentrator coupled to at least one of the intake ports, and a detector coupled to the concentrator. The horizontally oriented output airstreams and multiple intake ports provide a system that can rapidly screen multiple people for explosives and other substances.

The system is capable of screening a combination of persons and baggage and provides screening without subjecting people to large containment volumes of air. Referring to the drawings more particularly by reference numbers, FIG. 1A shows an embodiment of an open structure explosives trace detection system 100. The detection system 100 includes a series of output ports 102 and intake ports 104 of a housing 106. The output ports 102 direct output airstreams in a horizontal direction. The intake ports 104 are coupled to a manifold (not shown) that collects the sample. The system 100 includes a pump 108, a sample concentrator 110, and a detector 112. FIG. 1B shows one embodiment of the output ports 102 and the intake ports 104 of the housing 106.

In operation, one or more persons walk through a corridor 105 of the system 100. In one mode of operation the pump 108 continuously applies positive pressure to the output ports 102 and negative pressure to the intake ports 104 to pull air back into the housing 106. The system 100 can run with a continuous stream of air through the output ports 102 and continuous pull of air through the intake ports 104. Alternatively, the system 100 can also operate with pulsed air jets and intakes.

The method of operation is similar to ETPs that require a person to stand stationary during screening. The air jets create a turbulent flow around the person that loosens particles, residue, and compound contamination from the individuals clothing and skin. If the person is concealing an explosives or other illicit material such as drugs, small amounts of contamination would collect on the persons exterior. These contaminations are removed by the air jets and are collected in the air and passed through the intake ports 104. The air containing contamination is then collected in the sample concentrator 110. The alternating rows of output ports 102 and intake ports 104 ensure that individuals are efficiently screened and that the intake ports 104 are close to the output ports 102 to maximize efficient collection of the contaminated air volume.

It is assumed that a person will walk through the system 100 at normal speed. Another method is to use a conveyor belt to control the speed of passage through the screening system.

FIG. 2A shows an alternate embodiment 200a that has three focusing zones. Individuals may either walk through without stopping in the manner explained for the system shown in FIG. 1, or individuals can be instructed to stand at a focal zone. This system allows three people to be screened simultaneously, which is much more efficient than the current state of the art which scans people one at a time. Although three zones are shown and described, it is to be understood that the system 200a may have any number of zones.

Each focal zone may include two rows of output ports 202 and a center row for the intake ports 204. This ensures that the individual is screened all around the body and for efficient collection through the intake ports 204.

FIG. 2B shows an alternate embodiment of a single person screening system 200b that has output ports 212 and intake ports 214 in a housing 216. The system 200b also includes a foot pad 218 for locating where individuals are to stand relative to the housing 216. The footpad 218 may have a metal detector (not shown) to check for metal objects in shoes and the ankle area. Because the lower output ports 212 also screen shoes for explosives, the combination of the trace explosives screening and metal screening avoids the need for people to remove shoes, which would greatly improve the flow of traffic through the security system relative to existing systems. The system 200b can also have a turnstile or other gate or access control device 222 to prevent people from passing through the screening area 210b until they are cleared by the screening devices. Although a single person station is shown and described, it is to be understood that the system may be a multi-person station.

Figure 3:
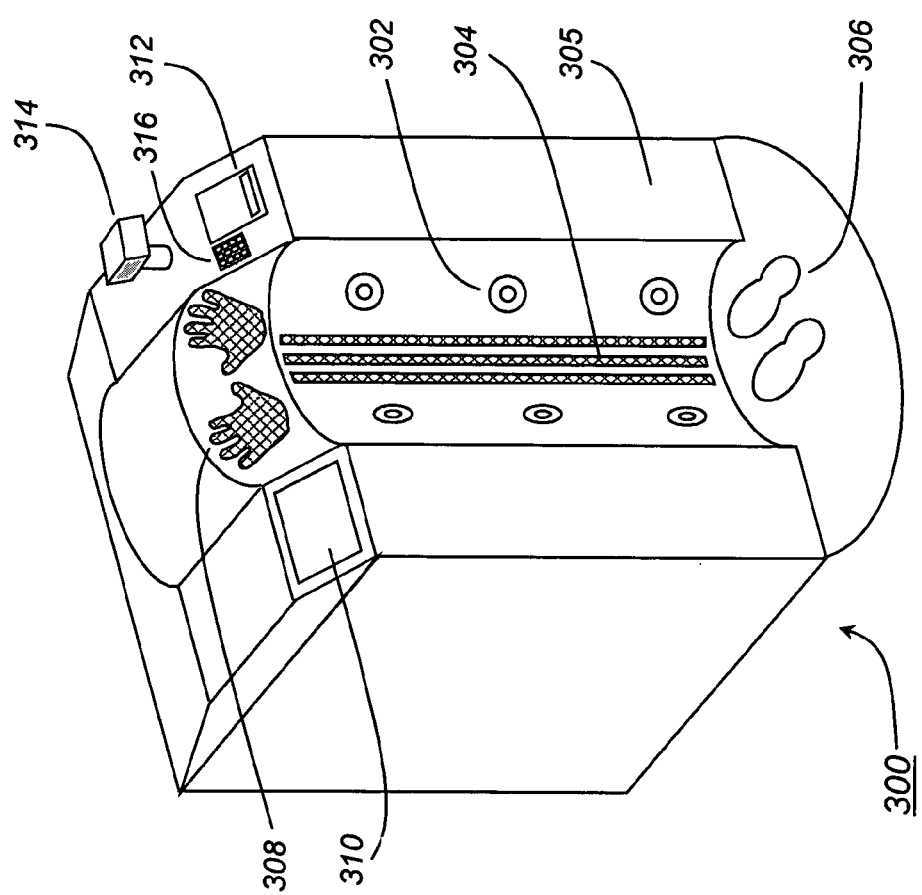
FIG. 3 is a perspective view showing a screening kiosk using air jets and intake ports for explosives screening and also contains a hand screener and a boarding pass reader.

FIG. 3 shows a screening kiosk 300 that has several screening methods and access control. A person can stand next to the unit and is then screened for contamination on the body in a manner similar to that described above, namely using airstreams from output ports 302 to dislodge contamination and an intake port/manifold assembly 304 to collect the contaminated air sample. The ports 302 and 304 are connected to a housing 305. Foot pads 306 instruct people where to stand and as described before, this platform can have a metal detector to screen for metal in shoes and the ankle area. The screening kiosk 300 may also have a hand screener 308. Hands tend to have the highest levels of contamination compared to other parts of the body. The screening kiosk 300 may also have a computer monitor 310 to instruct people on the operation of the kiosk and/or can give results of the screen. The kiosk 300 can also have a document reader that consists of an insertion reader 312 which can be used to mark the document or issue a new document. A bar code reader 314 and a keypad 316 can also be integrated into the kiosk 300. The document may be a boarding pass or other means of passage. The device can either mark the document or issue a new document in order to certify that the person has been screened safely.

Figure 2:
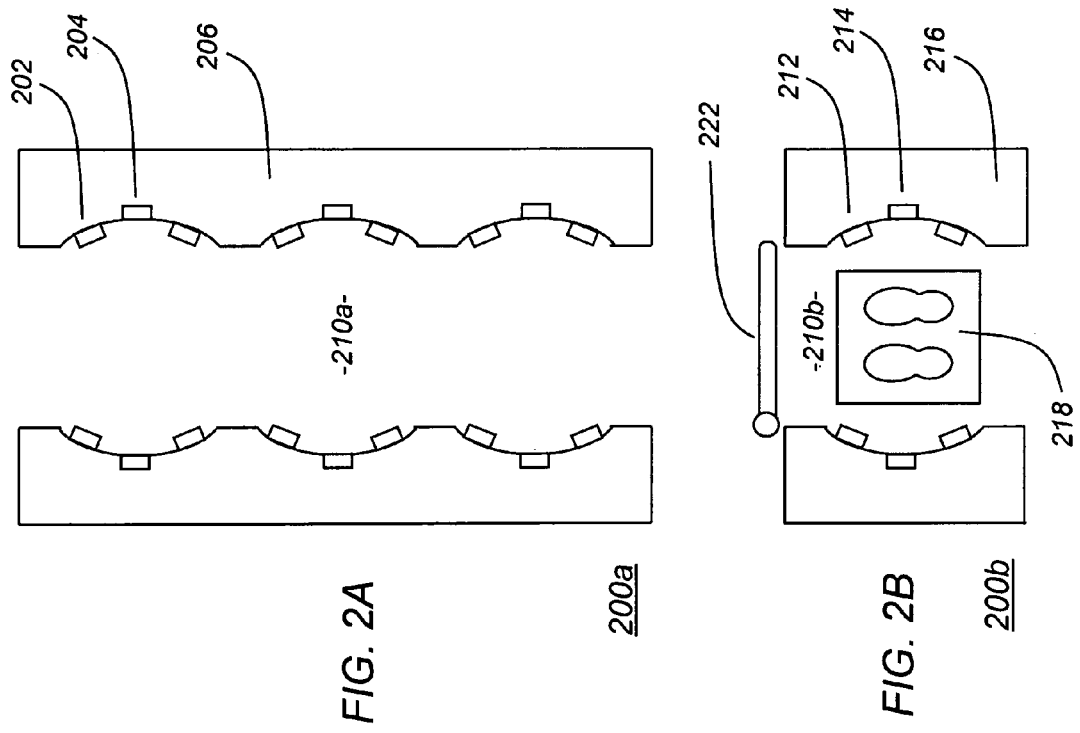
FIG. 2A is a top view of an alternate embodiment of the walk-through passageway that utilizes curved surfaces for the air jets and intake ports in order to define focusing zones.
FIG. 2B is a top view of a single individual walk-through explosives detector using air jets and intake ports and also incorporating a metal detector for shoes and a turnstile gate for exiting.

The screening devices in FIGS. 1-3 may also contain other detection capabilities such as a metal detector and radiation detector by prior art methods in order to further improve the utilization with respect to maintaining high throughput for persons and to minimize floor space.

Figure 4B:
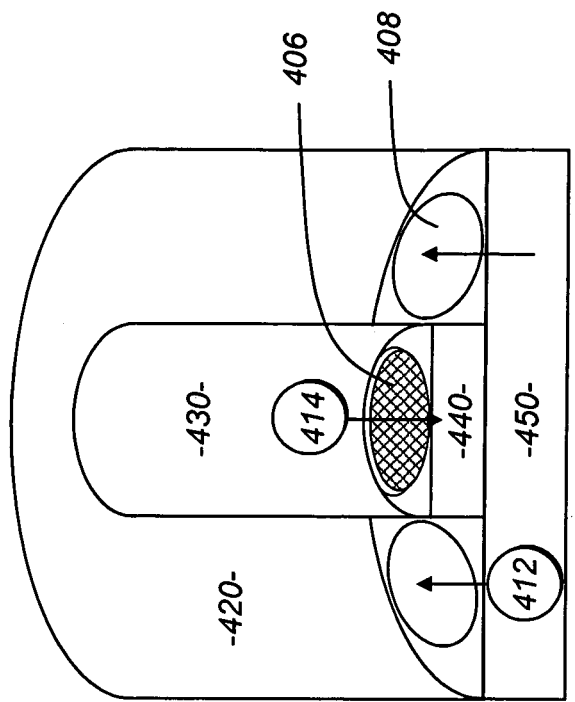
FIG. 4B is a side view of FIG. 4A illustrating the flow of air for the air jets and the intake manifold and system of explosives sample concentration.
Figure 4A:
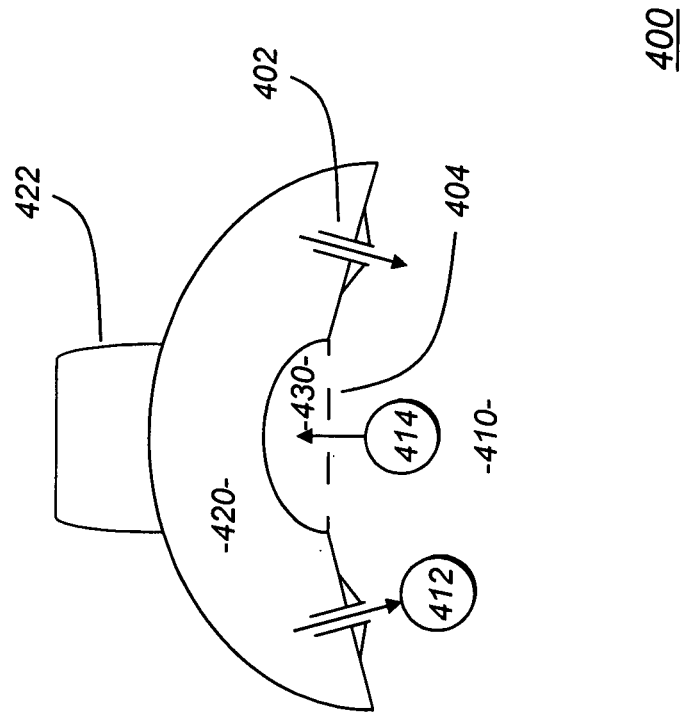
FIG. 4A is a top view illustrating the creation of air jets, and the pulling of a sample volume into the intake manifold.

FIG. 4A shows an embodiment of a system that includes output ports 402 and intake ports 404. The output ports 402 push air in a direction indicated by arrows 412 and the intake ports 404 pull in air in a direction indicated by arrows 414. The system includes a manifold 420 that stabilizes the positive pressure that is delivered to the output ports 402. The output ports 402 and intake ports 404 are coupled to a pump 422. FIG. 4B shows the flow of air 414 through the intake ports 404 entering an intake manifold region 430 that then leads through a concentrator device 406. The concentration device 406 can be a metal mesh that can capture particulate matter such as explosives and drugs, or may be another concentrator device such as that used to collect chemical vapor, or it may be a hybrid device that captures particles and vapor. The pump 422 can deliver a high pressure flow either directly to manifold region 420 or to another region 450 that has an open flow to region 420 through an opening 408. FIG. 4B also shows that the pump 422 draws flow 414 into a negative pressure region 440 that is connected to the pump.

FIG. 5A shows an embodiment of a hand screener that can be used to detect trace contamination of explosives or other illicit material such as drugs. The hand screener includes a grate 508 that is coupled to a spring 512 such that when hands depress the grate 508 and make contact with an electrical or other indicator 506, the pump is activated to provide air flow 512a through output ports 502a and intake flow 514a through the intake port/grate 508.

FIG. 5B shows an embodiment of a hand screener that does not require contact with a grate or other object. A person may insert their hands into an opening 510, wherein an indicator (not shown) such as a position detector can be used to sense that the hands are in a proper position. Upon detection, a pump (not shown) can turn on to provide the air flow 512b through output ports 502b and the intake flow 514b through the intake port.

Figure 6C:
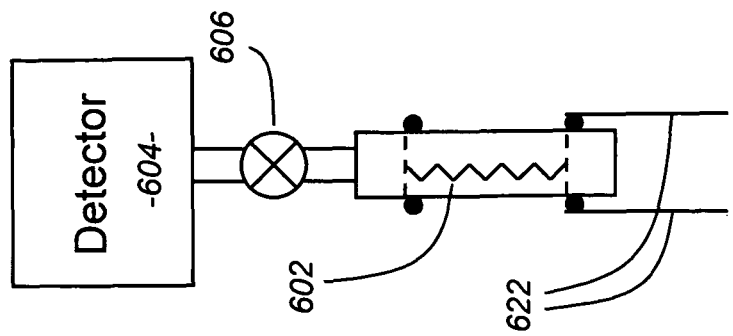
FIG. 6C is an illustration similar to FIG. 6B showing the mesh in an open position.
Figure 6B:
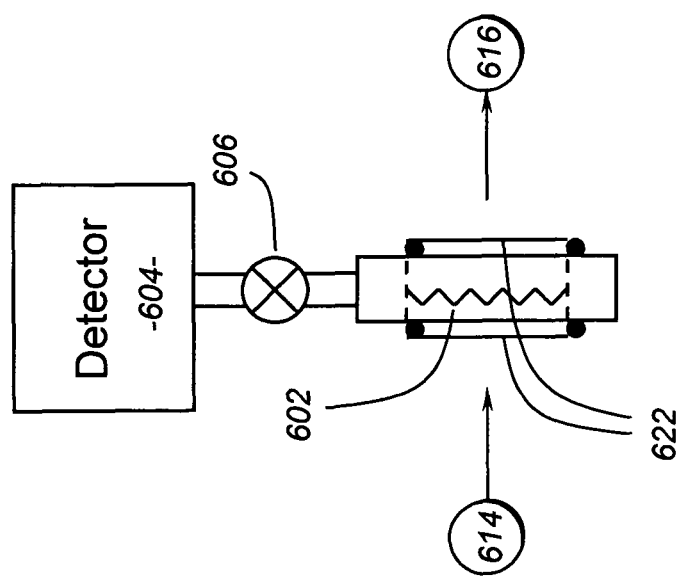
FIG. 6B is an illustration showing the flow of sample through the concentrator mesh and a method of closing a shutter to the mesh and opening a valve to the detector.
Figure 6A:
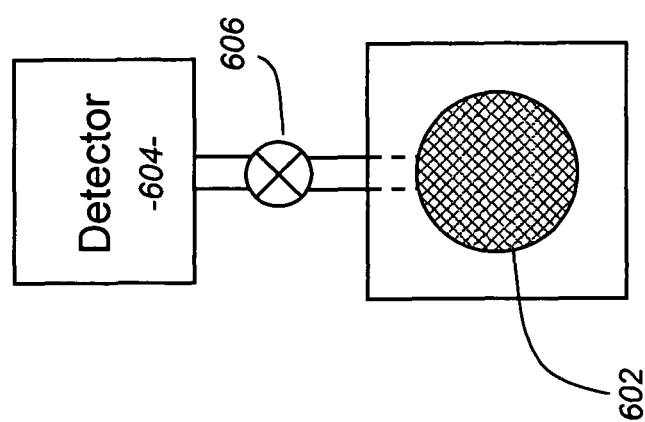
FIG. 6A is a schematic showing a concentrator mesh connected to a detector.

FIGS. 6A, 6B and 6C show a system where a sample is collected onto mesh or other concentrator 602 and then coupled to a detector 604. In the simplest configuration, the sample on mesh 602 is delivered to the detector 604 through a valve 606 that can be turned on and off. The concentrator mesh 602 must also be isolated from the main sampling collecting air flow 614 that is pulled through the mesh 602 by flow 616 to the pump as shown in FIG. 6B. This can be achieved using a shutter or gate valve 622, which is shown in closed and open positions in FIGS. 6B and 6C, respectively.

The use of multiple output ports and intake ports for the different embodiments of the open structure walk-through screening systems illustrated in FIGS. 1-3 can be used in a concentration and detection subsystem that has multiple concentrator devices, or a single detector in each assembly (e.g., 106, 206, 216). U.S. Pat. Appl. 2006/0196249 describes several embodiments of such switching devices and is hereby incorporated by reference.

Figure 7:
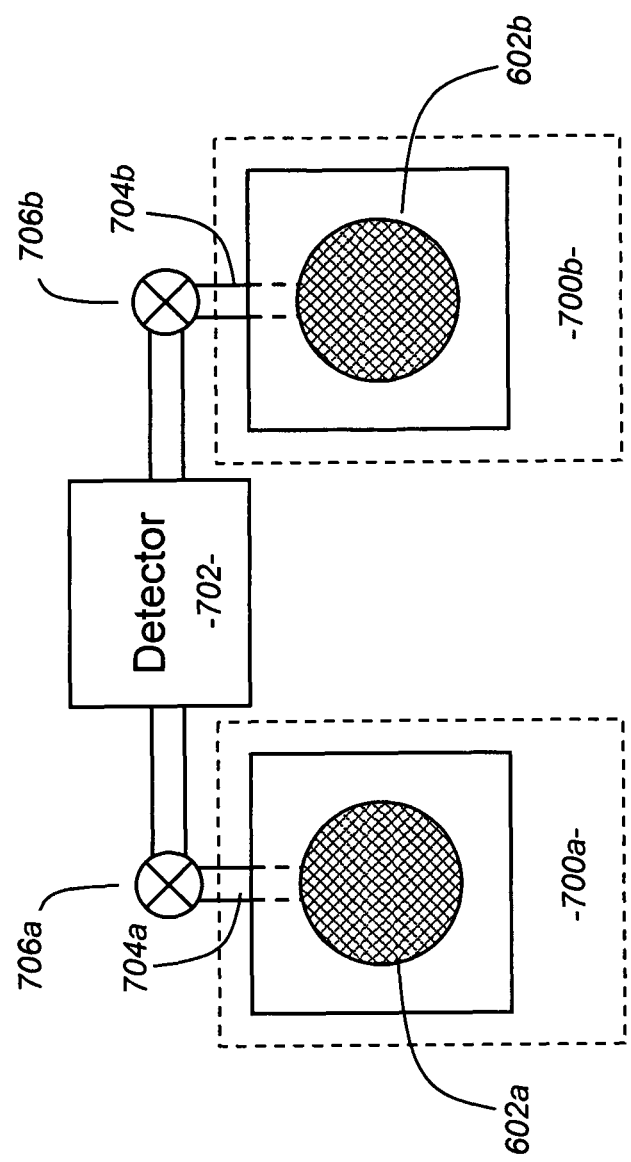
FIG. 7 is a schematic showing two concentrator mesh assemblies coupled to a single detector.

FIG. 7 shows an embodiment with two concentrator subassemblies 700a and 700b integrated to a single detector 702 through sample tubes 704a and 704b and valves 706a and 706b. In this configuration, the sample flow 614 and 616 shown in FIG. 6B can pass through one, or both, or neither of concentration meshes 602a and 602b depending on the position of the shutter 622 shown in FIGS. 6B and 6C. In normal operation valves 706a and 706b would be closed if the shutter 622 is open, which is the sample collection period, and the valves 706a and 706b would be open when the shutters 622 are closed, which is the sample detection period. During the latter period when sample is delivered to the detector 702, the meshes 602a and 602b are thermally heated to desorb and vaporize the collected sample on the mesh.

Figure 8:
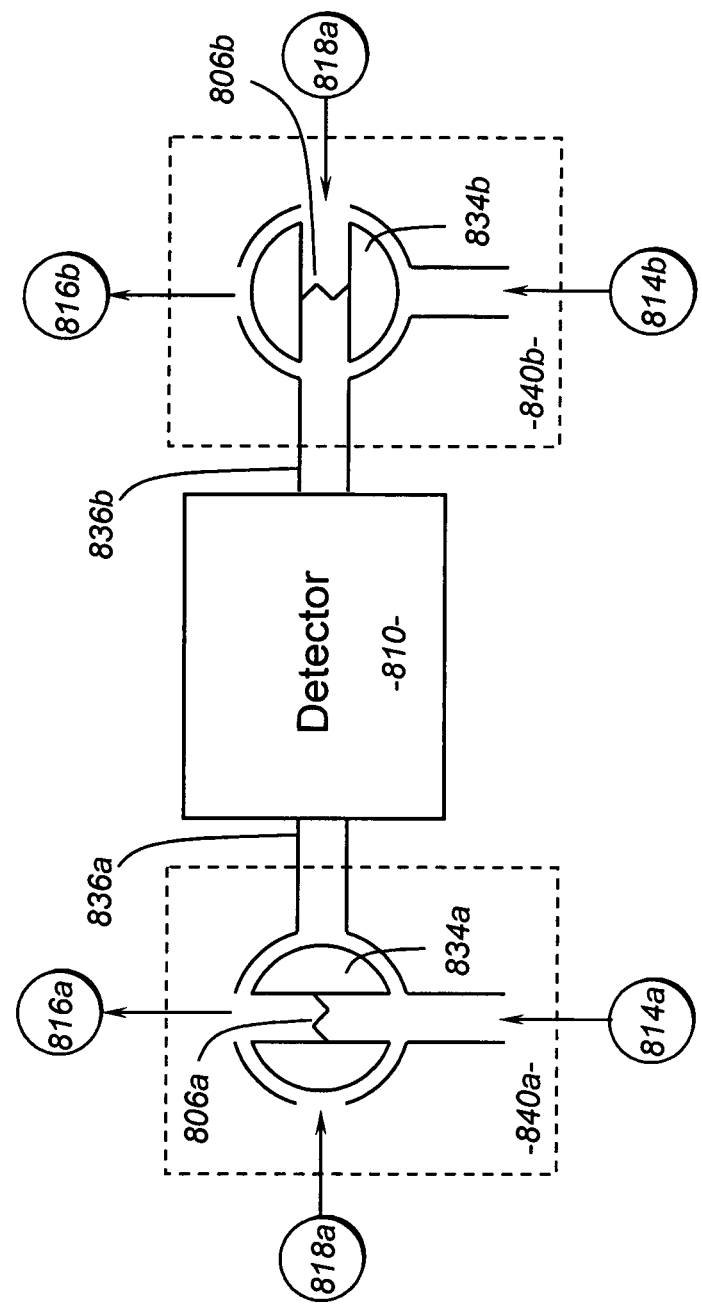
FIG. 8 is a schematic showing a sample concentrator switched from sample flow through the concentrator to delivery flow of desorbed sample to a detector; and, FIG. 9 is a schematic showing a particle concentrator device coupled to a sample concentrator and detector.

FIG. 8 shows another embodiment of a system for collecting sample on a concentrator mesh or substrate 806a and 806b and switching the mesh or substrate to the detector 810. The concentrator subassemblies 840a and 840b use rotary devices 834a and 834b, respectively, to rotate the meshes 806a and 806b from a position that accepts sample flow 814a and 814b by the pumping action 816a and 816b to a position that allows the meshes to deliver the sample to the detector through tubes 836a and 836b. A pick up flow is shown as 818a and 818b that directs the sample into the detector 810. The multiple concentrator subassemblies 840a and 840b can operate independently such that both, one or the other, or neither, can be in the sample collection state. However the preferred operation is one in which one mesh 806a or 806b is collecting sample and the other mesh 806b or 806a is delivering sample to the detector 810. U.S. Pat. Appl. 2006/0196249 discloses other systems for collecting sample and switching flows.

The systems described and shown in FIGS. 1-3 may have flow rates through the output ports and back into the intake ports that are significantly less than prior art systems. By way of example, a full body portal must circulate a full portal volume in a few seconds and typically have flow rates of about 500 L/s. A screening system such as the system shown and described in FIG. 3 requires about ⅟₁₀ the sampling volume and therefore a flow rate of about 50 L/s. This lower flow rate allows the use of a particle concentrator device such as a momentum impactor where a majority flow is diverted from the concentrator and a minor flow containing the predominance of particles flows to the concentrator.

Figure 9:
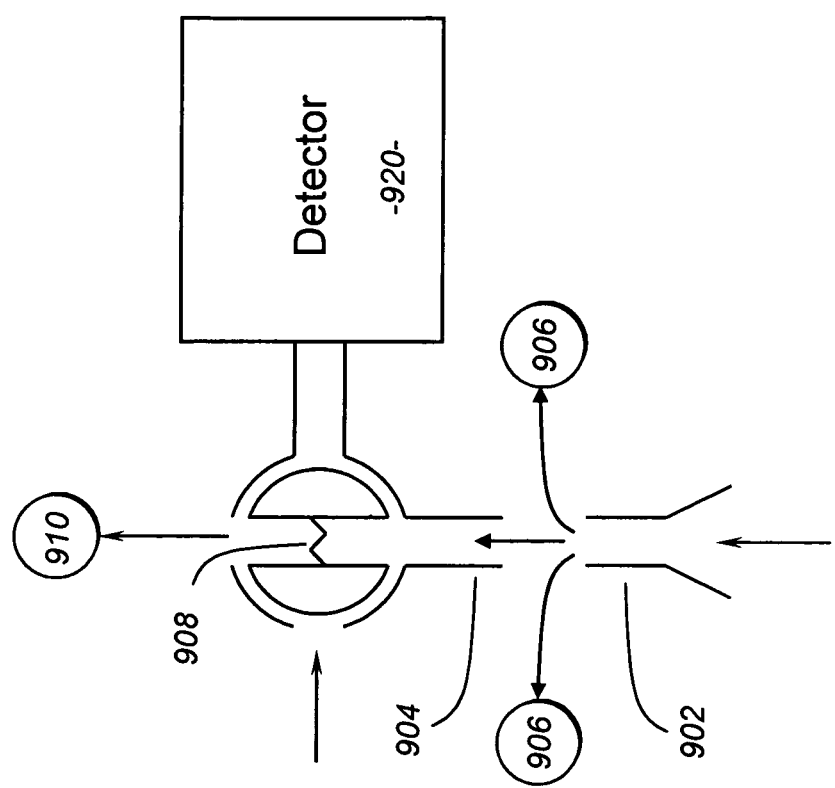

FIG. 9 shows an embodiment of a particle concentrator consisting of a major flow tube 902, and a minor flow tube 904 that uses a pumping flow 906 to divert the majority of the air flow. Particles cannot make the fast turn shown by pumping flow 906 and continue in the minor flow to inlet tube 902. The minor flow, which is enriched with particles, is then deposited on the concentrator mesh or substrate 908 with the assistance of a minor pumping flow 910. The advantage of this configuration is that a smaller concentrator mesh can be used and therefore the sample delivery flow to the detector 920 can be reduced, which leads to a more concentrated sample flow, which can lead to greater sensitivity.

The ability to independently switch multiple concentrator subassemblies enables a variety of modes of operation for the screening systems illustrated in FIGS. 1-3. The screening system 100 in FIG. 1 is intended to allow multiple people to walk through the screening region 110. In this case the output ports 102 can operate continuously and multiple concentrator subassemblies can be integrated with the multiple intake ports 104 such that one or more concentrators would be collecting sample and one or more concentrators would be delivering sample to the detector. It is also possible to have two or more concentrator subassemblies for each intake port 104 so that at least one concentrator is collecting sample at all times. The screening system 200a in FIG. 2A can operate as described above in a continuous walk-through mode. However another mode of operation is to have three people walk in and stand still while the air jets 202 and intake ports 204 are on. When screening is complete all three people can exit while analysis of the collected sample is performed. The analysis can be done in sequence, by delivering sample to the detector from one screening zone at a time. Retaining identification of which zone a detected compound came from may be employed in this method. For greater speed, all concentrators can deliver their sample to the detector; however, if there is an alarm, all three people would have to be screened again. In this latter case, one could use just one concentrator assembly for each unit 206 with all the intake manifolds 204 connected to the one concentrator.

The screening systems in FIGS. 1-3 can have additional sensors in addition to the explosives and drug trace detection screening disclosed herein. The screening systems 200b and 300 in FIGS. 2B and 3 show a metal detector for shoes and lower leg that can be integrated with any of the screening systems. A full body metal detector can also be included at the exit of each of the screening systems. Other sensors such as a nuclear/radiation detector can be integrated into the screening systems. These are conventional devices known in the prior art and which can be added without interfering with the basic functions of the explosives and drug trace detection screening systems.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for detecting a substance from a plurality of people, comprising:
   collecting a sample from each person of a plurality of people simultaneously comprising:
      moving the people into a portal that defines a plurality of focusing zones, wherein each focusing zone has a plurality of output ports and intake ports, and each focusing zone is configured for one person;
      directing a plurality of output airstreams from the output ports onto the people, inducing a turbulent air flow about the people, and collecting air from the people into the intake ports; and,
      capturing a substance on at least one concentrator of a plurality of concentrators,
   wherein each concentrator is coupled to at least one focusing zone;
   analyzing the sample; and,
   detecting the substance with at least one detector of a plurality of detectors, wherein one concentrator is coupled to the at least one detector.

2. The method of claim 1, wherein the intake ports are arranged in groups, each group having an associated concentrator, and sequentially coupling the concentrators to the detectors.

3. The method of claim 1, wherein the output airstreams continuously flow.

4. The method of claim 1, wherein the output airstreams are pulsed.

5. The method of claim 1, wherein the concentrator collects particle and vapor.

6. The method of claim 1, wherein the output ports are oriented to focus the output airstreams.

* * * * *

UNITED STATES PATENT AND TRADEMARK OFFICE
CERTIFICATE OF CORRECTION

| | |
|---|---|
| PATENT NO. | : 8,614,582 B2 |
| APPLICATION NO. | : 12/082535 |
| DATED | : December 24, 2013 |
| INVENTOR(S) | : Syage et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1243 days.

Signed and Sealed this
Twenty-first Day of April, 2015

Michelle K. Lee
*Director of the United States Patent and Trademark Office*